United States Patent [19]  [11] 3,954,870
Fukumaru et al.  [45] May 4, 1976

[54] METHOD OF RACEMIZATION OF OPTICALLY ACTIVE AMINES

[75] Inventors: Toshitsugu Fukumaru, Kyoto; Yoshio Suzuki, Amagasaki, both of Japan

[73] Assignee: Sumitomo Chemical Company, Limited, Osaka, Japan

[22] Filed: Feb. 28, 1972

[21] Appl. No.: 230,036

Related U.S. Application Data

[63] Continuation-in-part of Ser. No. 36,413, May 11, 1970, abandoned.

[52] U.S. Cl............................ 260/570.5 R; 252/472; 252/477 Q; 260/404; 260/566 R; 260/999
[51] Int. Cl.².................................... C07C 87/28
[58] Field of Search............... 260/570.5 R, 570.8 R

[56] References Cited
UNITED STATES PATENTS
2,797,243   6/1957   Hartgerink........................ 260/570.8

Primary Examiner—Robert V. Hines
Attorney, Agent, or Firm—Stevens, Davis, Miller & Mosher

[57] ABSTRACT

An optically active α,β-di-phenylethylamine of the formula,

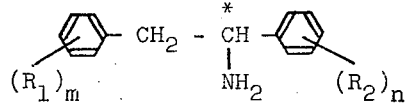

wherein $R_1$ and $R_2$ are each hydrogen or $C_1 - C_4$ alkyl and $m$ and $n$ are each an integer of 1 to 5, is racemized by heating the optically active amine at a temperature between 100°C and the boiling point of the amine in the presence of a dry Raney nickel catalyst in the atmosphere of inert gas. d-Isomers are more useful than the l-isomers as intermediates of optically active fatty acid amides having cholesterol lowering effects.

5 Claims, No Drawings

METHOD OF RACEMIZATION OF OPTICALLY ACTIVE AMINES

CROSS REFERENCE TO RELATED APPLICATIONS

This is a continuation-in-part of co-pending application Ser. No. 36,413 filed on May 11, 1970 and is now abandoned.

The present invention relates to a method for racemizing optically active α,β-diphenylethylamines. More particularly this invention pertains to a method for racemizing optically active α,β-diphenylethylamines of the formula,

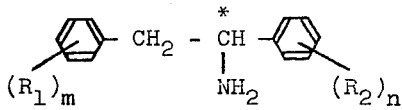

wherein $R_1$ and $R_2$ are each hydrogen, or $C_1 - C_4$ alkyl (e.g., methyl, ethyl, n- or iso-propyl or n-, iso- or t-butyl) and $m$ and $n$ are each an integer of 1 to 5.

The present inventors previously found a process for optically resolving some of α,β-diphenylethylamines of the above-mentioned formula, and that optically active fatty acid amides derived from the resolved d-amines are superior to those derived from the l-amines in anti-atherosclerosis action.

It has been known that optically active amines are racemized on the treatment with alkaline solutions, alkaline catalysts such as alkali metals (U.S. Pat. No. 3,168,566), alkali alkoxides, aluminum alkoxide and Lewis acid and reduction catalysts such as Raney nickel catalyst (U.S. Pat. No. 2,797,243). In the case of the racemization of α,β-diphenylethylamines of the above-mentioned formula, however, it has been difficult to racemize them in a high yield on such known treatment. That is, the treatment of the optically active α,β-diphenylethylamines with such alkaline catalysts of prior art have resulted in the formation of neutral impurities and other by-products and the optically active amines have not been well racemized. On the other hand, Raney nickel catalyst containing alcohol or water has been used as the catalyst for the racemization reaction.

In the case of the racemization of the optically active α,β-diphenylethylamines with alcohol-replaced Raney nickel catalyst (U.S. Pat. No. 2,797,243), the racemization reaction velocity is too low and the racemization reaction is not complete and produces a lot of by-products such as ketimine derivative, secondary amine and others. On the contrary, the present inventors have found that the optically active α,β-diphenylethylamines can be advantageously racemized by heating in the presence of a dry Raney nickel catalyst in the atmosphere of an inert gas.

The dry Raney nickel catalyst is prepared by drying usual Raney nickel catalyst which contains water or alcohol. The drying of the Raney nickel catalyst is accomplished by the following procedures:
a. Azeotropic method (See (a) of Example 2)
b. Distillation method (See (b) of Example 2)

The activity of the dry Raney nickel catalyst is high. Therefore, when the dry Raney nickel catalyst is used, the reaction time of the racemization is short and the formation of undesired by-products can be prevented.

Accordingly an object of the present invention is to provide a novel and improved method for racemizing optically active α,β-diphenylethylamines of the above-mentioned formula. Other objects and merits of the present invention will be apparent from the following descriptions.

In order to accomplish these objects the present invention provides a method for racemizing optically active α,β-diphenylethylamines of the formula.

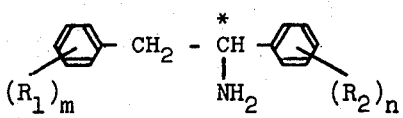

wherein $R_1$ and $R_2$ are each hydrogen or $C_1 - C_4$ alkyl and $m$ and $n$ are each an integer of 1 to 5, which comprises heating an optically active α,β-diphenylethylamine of the above-mentioned formula in the presence of an effective amount of a dry Raney nickel catalyst in the atmosphere of inert gas at a temperature between 100°C and the boiling point of the said α,β-diphenylethylamine for a period of time between several minutes and a few hours.

Optically active α,β-diphenylethylamines to be racemized in the method of the present invention are obtained by the optical resolution of the optically inactive amines according to a method disclosed, for example, in our co-pending Japanese Patent application No. 37208/1969. These optically active amines are usable regardless of the extend of optical purity.

In the preparation of the dry Raney nickel catalyst, the Raney nickel catalyst obtained by leaching Raney alloy according to the method of W-3 or W-4 may be used.

The amount of the catalyst is not particularly limited. Even when the catalyst is used in a large amount, no side reaction is enhanced, and on the other hand, if the catalyst is used in a remarkedly small amount, the reaction time may be prolonged.

In the method of the present invention, the catalyst used is scarcely consumed and hence can be repeatedly used to bring about marked industrial advantages.

The racemization of the present invention is carried out in the atmosphere of an inert gas in order to avoid the deactivation of the catalyst and the formation of carbonate due to the reaction of the α,β-diphenylethylamine with air, and the formation of other by-products. Examples of the inert gas include nitrogen, helium or ammonia gas or a mixture thereof. The use of hydrogen gas tends to promote the catalytic reduction of the α,β-diphenylethylamines and the formation of by-products such as secondary amine and others and hence is not desirable. When the above-mentioned inert gas is used in a tightly sealed state, the extent of racemization can be enhanced rather than in the case where it is flowed as a current of the gas during the reaction. Even if the inert gas is used in a tightly sealed state, the increase of temperature and the increase of inner pressure due to ammonia generated by a side reaction are so slight that there occurs no problem from the standpoint of apparatus.

The racemization of the present invention requires a temperature between 100°C and the boiling point of the optically active α,β-diphenylethylamine to be racemized and a period of time between several minutes and a few hours. At a lower temperature within the said range, a longer period to time is required for a satisfactory racemization. The treatment for a longer period of time than the said range results in increasing the amount of by-products such as the ketimine derivative of the formula,

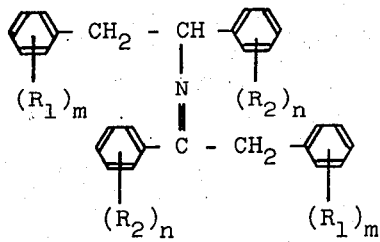

wherein $R_1$, $R_2$, $m$ and $n$ are as defined above, and the ketimine derivative having the reverse specific rotary powers to those of the optically active amines, and it results in increasing impurities and in lowering the yield of the objective racemized amines. Accordingly, it is preferable to carry out the racemization at a temperature of 140°–150°C for several minutes to several tens minutes.

Examples of optically active amines which can be racemized in the present invention include:

l- or d-$\alpha,\beta$-diphenylethylamine
l- or d-$\beta$-(p-, o- or m-tolyl)-$\alpha$-phenylethylamine
l- or d-$\beta$-(p-, o- or m-ethylphenyl)-$\alpha$-phenylethylamine
l- or d-$\beta$-[p-, o- or m-(n- or i-)-propylphenyl]-$\alpha$-phenylethylamine
l- or d-$\beta$-[p-, o- or m-(n-, i- or t-)-butylphenyl]$\alpha$-phenylethylamine
l- or d-$\beta$-phenyl-$\alpha$-(p-, o- or m-tolyl)ethylamine
l- or d-$\beta$-phenyl-$\alpha$-(p-, o- or m-ethylphenyl) ethylamine
l- or d-$\beta$-phenyl-$\alpha$-[p-, o- or m-(n- or i-)-propylphenyl]ethylamine
l- or d-$\beta$-phenyl-$\alpha$-[p-, o- or m-(n-, i- or t-)-butylphenyl]ethylamine
l- or d-$\beta$-(p-, o- or m-tolyl)-$\alpha$-(p-, o- or m-tolyl)ethylamine
l- or d-$\beta$-(p-, o- or m-tolyl)-$\alpha$-(p-, o- or m-ethylphenyl)ethylamine
l- or d-$\beta$-(p-, o- or m-tolyl)-$\alpha$-[p-, o- or m-(n- or i-)-propylphenyl]ethylamine
l- or d-$\beta$-(p-, o- or m-tolyl)-$\alpha$-[p-, o- or m-(n-, i- or t-)-butylphenyl]ethylamine
l- or d-$\beta$-(p-, o- or m-ethylphenyl)-$\alpha$-(p-, o- or m-ethylphenyl)ethylamine
l- or d-$\beta$-(p-, o- or m-ethylphenyl)-$\alpha$-(p-, o- or m-tolyl)ethylamine
l- or d-$\beta$-(p-, o- or m-ethylphenyl)-$\alpha$-[p-, o- or m-(n- or i-)-propylphenyl]ethylamine
l- or d-$\beta$-(p-, o- or m-ethylphenyl)-$\alpha$-[p-, o- or m-(n-, i- or t-)-butylphenyl]ethylamine
l- or d-$\beta$-[p-, o- or m-(n- or i-)-propylphenyl]-$\alpha$-(p-, o- or m-tolyl)ethylamine
l- or d-$\beta$-[p-, o- or m-(n- or i-)-propylphenyl]-$\alpha$-(p-, o- or m-ethylphenyl)ethylamine
l- or d-$\beta$-[p-, o- or m-(n- or i-)-propylphenyl]-$\alpha$-[p-, o- or m-(n- or i-)-propylphenyl]ethylamine
l- or d-$\beta$-[p-, o- or m-(n-or i-)-propylphenyl]-$\alpha$-[p-, o- or m-(n-, i- or t-)-butylphenyl]ethylamine
l- or d-$\beta$-[p-, o- or m-(n-, i- or t-)-butylphenyl]-$\alpha$-(p-, o- or m-tolyl)ethylamine
l- or d-$\beta$-[p-, o- or m-(n-, i- or t-)-butylphenyl]-$\alpha$-(p-, o- or m-ethylphenyl)ethylamine
l- or d-$\beta$-[p-, o- or m-(n-, i- or t-)-butylphenyl]-$\alpha$-[p-, o- or m-(n- or i-)-propylphenyl]ethylamine
l- or d-$\beta$-[p-, o- or m-(n-, i- or t-)-butylphenyl]-$\alpha$-[p-, o- or m-(n-, i- or t-)-butylphenyl]-ethylamine and their polysubstituted compounds in which the abovementioned substituents have been mixed each other.

The optically inactive $\alpha,\beta$-diphenylethylamines which are racemized in high yield by the present method are again subjected to optical resolution to obtain their optically active amines.

The present method is illustrated in further detail below with reference to examples. However, it should be understood that the present invention is not limited to the examples.

EXAMPLE 1

Preparation of Usual Raney Nickel Catalyst a. Raney nickel catalyst was prepared by leaching a Raney alloy with a caustic alkali according to a method as described in H. Adkins and A. A. Pavlic, J. Am. Chem. Soc., Vol. 68, page 1471 (1946) and ibid., Vol. 69, page 3039 (1947) and washing the resulting catalyst with water.

b. The thus obtained Raney nickel catalyst was washed three times with each 2.5 times the weight of the catalyst of 95% ethanol and 5–7 times with each 2.5 times the weight of the catalyst of 99% ethanol to replace the water contained therein by the alcohol.

EXAMPLE 2

Preparation of Dry Raney Nickel Catalyst of the Present Application a. Azeotropic method:

A four-necked flask equipped with a stirrer, a thermometer, a dropping funnel and a water separator was filled with nitrogen gas. The equipment was sealed with nitrogen gas to prevent the invasion of air. The Raney nickel catalyst as prepared in (a) of Example 1 and an amount of toluene enough to sufficiently immerse the catalyst were entered in the flask and the contents were stirred with heating. The water distilled off as the toluene azeotrope was separated out. The temperature of the contents was first lower than the boiling point of toluene and became the same as the boiling point of toluene after one or two hours. Then, the bath temperature was gradually increased to a temperature of 20°–40°C higher than the boiling point of the solvent. At the temperature, the reaction mixture was refluxed for one to three hours to further remove water. Finally, the solvent was distilled off until an amount of 2–4 times the weight of the catalyst.

b. Method of distillation under reduced pressure:

A reaction flask connected to an apparatus for distillation under reduced pressure was filled with nitrogen gas. The alcohol-replaced Raney nickel catalyst as prepared in (b) of Example 1 was entered in the flask. The alcohol was distilled off under weakly reduced pressure, and finally the alcohol was completely distilled off at a temperature of 80°–100°C/10–40 mmHg for 0.5 to 2 hours. Heating was then stopped and nitrogen gas was introduced into the flask to increase the pressure to ordinary pressure when the temperature was reduced to room temperature.

EXAMPLE 3

A mixture comprising 50 g of l-α-phenyl-β-(p-tolyl)-ethylamine ($[\alpha]_D^{20}$ −9.02°) and 5 g of dry Raney nickel catalyst as prepared in (b) of Example 2 was heated with stirring at 145°–150°C for 1 hour in a sealed vessel filled with nitrogen gas. The reaction mixture was filtered to remove the Raney nickel catalyst, which was washed with 50 ml of toluene. All of the filtrate and washing were combined and concentrated. The resultant residue was distilled under reduced pressure. The desirable product of racemized α-phenyl-β-(p-tolyl)-ethylamine was obtained, yield: 46.5 g, b.p. 125°–127°C/0.3 mmHg, $[\alpha]_D^{20}$ −0.35°, $N_D^{24}$ 1.5731.

| Infrared absorption spectrum: | Coincided with the starting material. |
|---|---|
| N.M.R. spectrum: | Reasonable |

Elementary analysis: Calculated (%) C: 85.26, H: 8.11, N: 6.63. Found (%) C: 85.34, H: 8.20, N: 6.51.

EXAMPLES 4–12

According to the manner similar to that in Example 3, optically active α-phenyl-β-p-tolyl-ethylamine was racemized under the conditions as set forth in Table 1. The results are shown in Table 1.

| Infrared absorption spectrum: | Coincided with that of the starting material. |
|---|---|

Elementary analysis: Calculated (%) C: 85.23, H: 7.66, N: 7.10. Found (%) C: 85.12, H: 7.39, N: 6.92.

EXAMPLE 14

A mixture comprising 20 g of d-α,β-diphenylethylamine ($[\alpha]_D^{20}$ +15.3°) and 3 g of dry Raney nickel catalyst as prepared in (a) of Example 2 was heated with stirring at 155°–160°C for 2 hours in sealed vessel filled with ammonia gas. Subsequently, the treatment similar to that in Example 3 was repeated. The desirable product of racemized α,β-diphenylethylamine was obtained, 16.1 g, b.p. 114°–116°C/0.8 mmHg, $[\alpha]_D^{23}$ +0.51°, $n_D^{30}$ 1.5780.

| Infrared absorption spectrum: | Coincided with the starting material |
|---|---|
| N.M.R. spectrum: | Reasonable |

Elementary analysis: Calculated (%) C: 85.23, H: 7.66, N: 7.10. Found (%) C: 85.37, H: 7.81, N: 7.00.

EXAMPLE 15

Table 1

| Example No. | Starting amine $[\alpha]_D^{20°}$ | Weight (g) | Catalyst Raney nickel (g) | Reaction Temp. (°C) | Time (hr) | Yield (g) | Boiling point (°C/mmHg) | $N_D$ | $[\alpha]_D^°$ |
|---|---|---|---|---|---|---|---|---|---|
| 4 | −8.26 | 30 | 1.2 | 150 | 1/6 | 28.5 | 125–127/0.3 | $n_D^{24}$ 1.5731 | $[\alpha]_D^{23}$ −0.42 |
| 5 | −8.85 | 10 | 0.5 | 140–150 | 1/3 | 9.3 | 120–123/0.07 | $n_D^{23}$ 1.5734 | $[\alpha]_D^{23}$ −0.46 |
| 6 | −8.26 | 50 | 2.5 | 140–150 | 1 | 45.9 | 124–127/0.3 | $n_D^{20}$ 1.5740 | $[\alpha]_D^{21}$ −0.65 |
| 7 | −8.26 | 50 | Recovered EXP. 5 2.5 | 140–150 | 2 | 43.2 | 127–129/0.4 | $n_D^{25}$ 1.5725 | $[\alpha]_D^{27}$ −0.51 |
| 8 | −12.5 | 10 | 1 | 145–150 | 1/3 | 9.2 | 127–129/0.4 | $n_D^{22}$ 1.5739 | $[\alpha]_D^{23}$ −0.32 |
| 9 | −11.7 | 20 | 2 | 160–165 | 1/4 | 18.6 | 119–122/0.06 | $n_D^{21}$ 1.5739 | $[\alpha]_D^{22}$ −0.41 |
| 10 | −8.26 | 30 | 1.5 | 130 | 3 | 27.5 | 124–128/0.3 | $n_D^{25}$ 1.5726 | $[\alpha]_D^{30}$ −0.82 |
| 11 | +12.7 | 20 | 4 | 145–150 | 1 | 18.7 | 116–119/0.05 | $n_D^{23}$ 1.5732 | $[\alpha]_D^{24}$ +0.10 |
| 12 | +9.6 | 20 | 5 | 140–145 | 2 | 17.6 | 121–124/0.01 | $n_D^{20}$ 1.5741 | $[\alpha]_D^{23}$ +0.21 |

| Example No. | Reaction product Elementary analysis | | | | | |
|---|---|---|---|---|---|---|
| | C % Calcd. | Found | H % Calcd. | Found | N % Calcd. | Found |
| 4 | 85.26 | 85.30 | 8.11 | 8.01 | 6.63 | 6.44 |
| 5 | 85.26 | 85.14 | 8.11 | 8.19 | 6.63 | 6.52 |
| 6 | 85.26 | 85.29 | 8.11 | 8.25 | 6.63 | 6.38 |
| 7 | 85.26 | 85.09 | 8.11 | 8.22 | 6.63 | 6.50 |
| 8 | 85.26 | 85.20 | 8.11 | 8.31 | 6.63 | 6.59 |
| 9 | 85.26 | 85.19 | 8.11 | 8.20 | 6.63 | 6.52 |
| 10 | 85.26 | 85.42 | 8.11 | 8.35 | 6.63 | 6.47 |
| 11 | 85.26 | 85.31 | 8.11 | 8.29 | 6.63 | 6.53 |
| 12 | 85.26 | 85.29 | 8.11 | 8.22 | 6.63 | 6.60 |

EXAMPLE 13

A mixture comprising 10 g of l-α,β-diphenylethylamine ($[\alpha]_D^{22}$ = −9.55°) and 300 mg of dry Raney nickel catalyst as prepared in (a) of Example 2 was heated with stirring at 140°–150°C for 1 hour in a sealed vessel filled with nitrogen gas. Subsequently, the treatment similar to that in Example 3 was repeated to obtain 9.1 g of racemized α,β-diphenylethylamine, b.p. 114°–116°C10.8 mmHg, $[\alpha]_D^{23}$ −0.51°, $n_D^{30}$ 1.5780.

A mixture comprising 10 g of l-α-(p-tolyl)-β-phenylethylamine ($[\alpha]_D^{20}$ −15.2°) and 1 g of dry Raney nickel catalyst was heated with stirring at 160°C for 2 hours in a sealed vessel filled with nitrogen gas. The reaction mixture was filtered to remove the Raney nickel catalyst, which was washed with 30 ml of ether. All of the filtrate and washings were combined and, concentrated. The resultant residue was distilled under reduced pressure. The desirable product of racemized α-(p-tolyl)-β-phenyl-ethylamine was obtained, 8.2 g, b.p. 112°–114°C/0.08 mmHg, $[\alpha]_D^{20}$ —0.71°, $N_D^{23}$ 1.5716.

| Infrared absorption spectrum: | Coincided with the starting material |
|---|---|

Elementary analysis: Calculated (%) C: 85.26, H: 8.11, N: 6.63. Found (%) C: 85.33, H: 7.99, N: 6.49.

What is claimed is:

1. A method for racemizing optically active $\alpha,\beta$-diphenylethylamines of the formula, $$(R_1)_m\text{-C}_6H_4\text{-CH}_2\text{-}\overset{*}{C}H(NH_2)\text{-C}_6H_4\text{-}(R_2)_n$$

wherein $R_1$ and $R_2$ are each hydrogen or $C_1 - C_4$ alkyl and $m$ and $n$ are each an integer of 1 to 5, which comprises heating an optically active $\alpha,\beta$-diphenylethylamine of the above-mentioned formula in the presence of an effective amount of a dry Raney nickel catalyst in the atmosphere of an inert gas at a temperature between 100°C and the boiling point of the said $\alpha,\beta$-diphenylethylamine for a period of time between several minutes and several hours.

2. A method according to claim 1, wherein the inert gas is nitrogen, helium, or ammonia gas.

3. A method according to claim 1, wherein the heating is carried out at a temperature between 140° and 150°C for a period of time between several minutes and several tens minutes.

4. A method according to claim 1, wherein the heating is carried out in a tightly sealed state.

5. A method according to claim 1, wherein the $\alpha,\beta$-diphenylethylamine is $\beta$-p-tolyl-$\alpha$-phenylethylamine, $\alpha$-p-tolyl-$\beta$-phenylethylamine or $\alpha,\beta$-diphenylethylamine.

* * * * *